United States Patent
Earle et al.

(10) Patent No.: US 7,094,925 B2
(45) Date of Patent: Aug. 22, 2006

(54) OXIDATION OF ALKYL-AROMATIC COMPOUNDS

(75) Inventors: Martyn John Earle, Belfast (GB); Suhas Prabhakar Katdare, Belfast (GB)

(73) Assignee: The Queen's University of Belfast, Belfast (GB)

( * ) Notice: Subject to any disclaimer, the term of this patent is extended or adjusted under 35 U.S.C. 154(b) by 0 days.

(21) Appl. No.: 10/398,532

(22) PCT Filed: Oct. 5, 2001

(86) PCT No.: PCT/GB01/04426

§ 371 (c)(1),
(2), (4) Date: Jun. 16, 2003

(87) PCT Pub. No.: WO02/30862

PCT Pub. Date: Apr. 18, 2002

(65) Prior Publication Data

US 2004/0015009 A1    Jan. 22, 2004

(30) Foreign Application Priority Data

Oct. 10, 2000    (GB) .................................. 0024745.2

(51) Int. Cl.
*C07C 51/16* (2006.01)
*C07C 45/28* (2006.01)
*C07C 27/00* (2006.01)

(52) U.S. Cl. .................... 562/410; 562/411; 562/412; 568/320; 568/432; 568/815

(58) Field of Classification Search ................ 562/410, 562/411, 412; 568/320, 432, 815
See application file for complete search history.

(56) References Cited

U.S. PATENT DOCUMENTS 2,993,070 A * 7/1961 Hopff ......................... 562/409
3,124,611 A * 3/1964 Shipman .................... 562/411
3,310,581 A * 3/1967 Mares ........................ 562/410
5,705,705 A * 1/1998 Brown et al. ............... 568/430

FOREIGN PATENT DOCUMENTS

DE    199 01 524 A    7/2000
WO    WO 00 32572 A    6/2000

OTHER PUBLICATIONS

The Merck Index, 11th Edition, 1989; 2228, 5552, 8598.*
Harustiak et al. Kinetics and Mechanism of Phase-Transfer Catalyzed Oxidation of p-Xylene by Molecular Oxygen. Journal of Molecular Catalysis, 1988, vol. 48, p. 335-342.*
Earle et al. Paradigm Confirmed: The First Use of Ionic Liquids to Dramatically Influence the Outcome of Chemical Reactions. Organic Letters, 2004, vol. 6 (5), p. 707-710.*

* cited by examiner

*Primary Examiner*—Johann R Richter
*Assistant Examiner*—Sikarl A. Witherspoon
(74) *Attorney, Agent, or Firm*—Drinker Biddle & Reath LLP; Daniel A. Monaco

(57) ABSTRACT

A process for the oxidation of an alkyl-aromatic compound, wherein the aromatic compound is admixed with an oxidising agent or sulfur compound in the presence of an ionic liquid is described. In this process, air, dioxygen, peroxide, superoxide, any other form of active oxygen, nitrite, nitrate, nitric acid or other oxides (or oxyhalides) of nitrogen (hydrate or anhydrous) are preferably used as the oxidising agent. The process is usually under Bronsted acidic conditions. The product of the oxidation reaction is preferably a carboxylic acid or ketone or an intermediate compound in the oxidation such as an aldehyde, or alcohol. The oxidation is preferably performed in an ionic liquid containing an acid promoter such as methanesulfonic acid.

27 Claims, No Drawings

OXIDATION OF ALKYL-AROMATIC COMPOUNDS

This invention relates to a process for the oxidation of aromatic compounds such as toluene and xylene. The oxidation of compounds such as toluene and xylene are important reactions and are carried out on a large scale. The products of the oxidation reactions, e.g. terephthalic acid, are widely used in the polymer industry.

Various methods exist for the oxidation of toluene, including oxidation with dioxygen, using a cobalt(III)[1,2] catalyst, periodate,[3] air using $Cs_5[SiW_{11}O_{39}Ru(III)(H_2O)]\cdot 7H_2O$ as a catalyst (59% yield).[4] hypochlorite catalysed by Ru(VIII) oxide tetroxide in $[Bu_4N]Br$.[5] These methods work well, but require either stoicheiometric quantities of oxidising agent or require special catalysts.

We have developed a procedure for the oxidation of alkylated aromatic compounds that either partially or completely oxidises the alkyl group to an alcohol, aldehyde, ketone or carboxylic acid.

Thus, according to one aspect of the present invention, there is provided a process for the oxidation of an alkyl-aromatic compound, wherein the aromatic compound is admixed with an oxidising agent or sulfur compound in the presence of an ionic liquid.

In this process, air, dioxygen, peroxide, superoxide, any other form of active oxygen, nitrite, nitrate, nitric acid or other oxides (or oxyhalides) of nitrogen (hydrated or anhydrous) are preferably used as the oxidising agent. The process is usually under Bronsted acidic conditions.

Preferably, the process involves the oxidation of the alkyl side chain of the aromatic compound in the presence of a nitrogen oxyacid species such as nitrate or nitric acid. This nitrogen(V) species oxidises the alkyl group, and is in turn reduced to a lower valent form of nitrogen. This lower valent form of nitrogen can be re-oxidised back to nitrogen(V) by means of an oxidising agent. Other oxidising agents suitable include dioxygen (air), oxygen, peroxides, superoxides.

Other suitable oxidating agents are certain sulfur compounds such as the sulfur acid/bases, eg $H_2SO_4$ or $H_2SO_3$.

This invention also allows for the separation of the ionic liquid and product by physical or chemical means such as distillation, steam distillation, azeotropic distillation, sublimation, gravity separation, solvent extraction, crystallisation, supercritical fluid extraction and chromatography.

Ionic liquids consist of two components, which are a positively charged cation and a negatively charged anion. Generally, any compound that meets the criterion of being a salt (consisting of an anion and cation) and is fluid at or near the reaction temperature or exists in a fluid state during any stage of the reaction may be defined as an ionic liquid.

The cation for the present process is preferably a 1,3-dialkylimidazolium cation such as 1-methyl-3-butylimidazolium. Other cations for this process are ammonium, pyrazolium, and other pyridinium, alkyl- or poly-alkylpyridinium, alkyl- or poly-alkyl phosphonium cations.

The anion for the process is preferably a sulfur-containing anion, such as sulfate, hydrogensulfate. Non-sulfur containing anions include those based on nitrogen, phosphorus, boron, silicon, selenium, tellurium, halogens, oxoanions of metals, and organic anions, such as trifluoroacetate, acetate, and anions that are arsenic, antimony, and bismuth based. The preferred anions are nitrate or methanesulfonate.

More than one ionic liquid or any combination of ionic liquids can be used in the present invention.

Suitable Process conditions.

Temperature: ideally 100–120° C. but to include 0° to 250° C.

Pressure: ideally, atmospheric, but include 1 mbar to 100 bar

Time: ideally 24–48 hours, can be 1 minute to 1 month.

The reaction preferably requires an acid to be present. This acid is generally an oxoacid of nitrogen, sulfur, selenium, tellurium, phosphorus, arsenic, antimony, or an organic acid anion (e.g. acetate, trifluoroacetate).

The oxidation of toluene is shown in scheme 1. As can be seen, the reaction can be carried out in [bmim] [OMs] ("OMs"=methanesulfonate) by the addition of nitric acid or in [bmim] [$NO_3$] by the addition of methanesulfonic acid.

Scheme 1.
The oxidation of toluene to benzene acid.

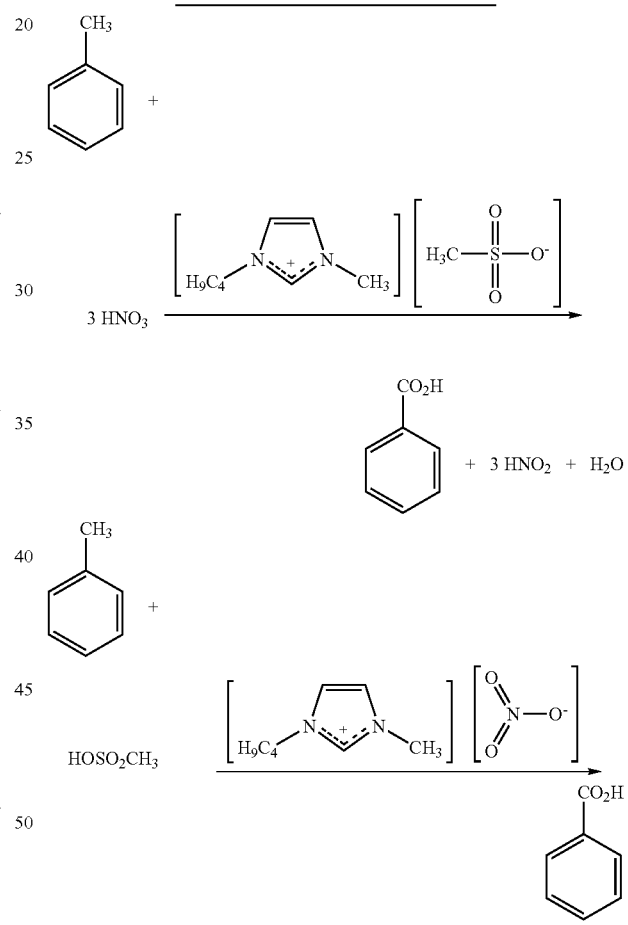

As the reaction proceeds, the nitrate or nitric acid (the oxidising agent) is believed to be reduced to nitrous acid, which is unstable under the acidic conditions employed in the reaction. This in turn is re-oxidised back to nitrate/nitric acid by an oxidising agent. The dioxygen in air will suffice, but other oxidants such as peroxides are also suitable.

The reaction can be carried out using a stoichiometric amount of nitric acid (or nitrate) or can be performed catalytically. In the latter case, if air is used to re-oxidise the nitrous acid formed in the reaction, the overall reaction is shown in scheme 2.

Scheme 2: The overall reaction for the oxidation of toluene in air.

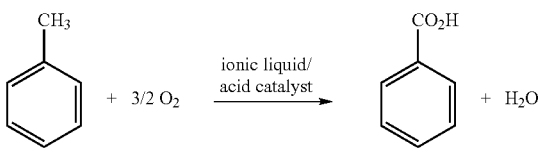

Other compounds oxidizable by this invention are o- or p-xylene, firstly to o- or p-toluic acid (2- or 4-methylbenzoic acid) then to, phthalic acid or terphthalic acids respectively. Ethylbenzene and n-propylbenzene can be oxidized under similar conditions to acetophenone and propiophenone as the major products. Also formed in these two reactions are benzoic acid, presumably from oxidative cleavage of the alkyl group.

The present invention is further illustrated with reference to the following Examples:

EXAMPLES

1. Oxidation of Toluene in [bmim] [OMs]

In a round-bottomed flask (25 cm$^3$) equipped with a magnetic stirrer flea and reflux condenser, 1-butyl-3-methylimidazolium methanesulfonate (0.23 g, 1 mmol) and toluene (0.18 g, 2 mmol) were added. 67% aqueous nitric acid (0.28 g, 3 mmol) was cautiously added and the mixture heated under reflux for 48 hours. The flask was cooled and the products analysed by gas chromatography. All of the toluene had reacted and signals due to benzoic acid (70% yield) and a by-product (2- and 4-nitrotoluene) were detected. The product(s) was isolated by Kugelrohr distillation at 5 mm Hg. This gave pale yellow oil (bp=100° C. at 5 mmHg) nitrotoluene and a colourless solid (bp=150° at 5 mmHg)—benzoic acid. The structures were confirmed by NMR analysis and were in accordance with authentic material.

2. Oxidation of Toluene in [bmim] [OMs]

In a round-bottomed flask (25 cm$^3$) equipped with a magnetic stirrer flea and reflux condensed, 1-butyl-3-methylimidazolium methanesulfonate (0.23 g, 1 mmol) and toluene (0.46 g, 5 mmol) were added. 67% aqueous nitric acid (0.18 g, 2 mmol) was cautiously added and the mixture heated under reflux for 48 hours. The flask was cooled and the products analysed by gas chromatography. All of the toluene had reacted and signals due to benzoic acid (90% yield) and a by-product product (2- and 4-nitrotoluene) were detected. The product(s) was isolated by Kugelrohr distillation at 5 mmHg. This gave pale yellow oil (bp=100° C. at 5 mmHg) nitrotoluene and a colourless solid (bp=150° at 5 mmHg)—benzoic acid. The structures were confirmed by NMR analysis and were in accordance with authentic material.

3. Oxidation of Toluene in [bmim] [NO$_3$]

In a round-bottomed flask (25 cm$^3$) equipped with a magnetic stirrer flea and reflux condensed, 1-butyl-3-methylimidazolium nitrate (0.23 g, 2 mmol) and toluene (0.46 g, 5 mmol) were added. 67% methanesulfonic acid (0.29 g, 3 mmol) was cautiously added and the mixture heated under reflux for 48 hours. The flask was cooled and the products analysed by gas chromatography. All of the toluene had reacted and signals due to benzoic acid (85% yield) and a by-product (2- and 4-nitrotoluene) were detected. The product(s) was isolated by Kugelrohr distillation at 5 mmHg. This gave pale yellow oil (bp=100° C. at 5 mmHg) nitrotoluene and a colourless solid (bp=150° at 5 mmHg)—benzoic acid. The structures were confirmed by NMR analysis and were in accordance with authentic material.

4. Oxidation of Ethylbenzene

In a 50 cm$^3$ round bottomed flask, equipped with a magnetic stirrer and reflux condenser, was added ethylbenzene (1.06 g, 10 mmol) and [bmim][OMs] (1.0 g). 67% Nitric acid (0.45 g, 5 mmol) was cautiously added and the mixture heated under reflux. After 48 hours the mixture was analysed by gas chromatography and found to contain 19% unreacted ethylbenzene, 23% benzoic acid and 57% acetophenone. The mixture was cooled and water (50 cm$^3$) was added. The products were extracted with diethyl ether (4×20 cm$^3$), concentrated on a rotary evaporator and purified by Kugelrohr distillation. This gave acetophenone (0.62 g, 51%) and benzoic acid (0.22 g, 18%).

5. Oxidation of p-xylene

In a 50 cm$^3$ round bottomed flask, equipped with a magnetic stirrer and reflux condenser, was added p-xylene (1.07 g, 10 mmol) and [bmim] [OMs] (2.0 g). 67% Nitric acid (0.90 g, 10 mmol) was cautiously added and the mixture heated under reflux. After 24 hours the mixture was analysed by gas chromatography (approximately 50% conversion), cooled and water (50 cm$^3$) was added. The resultant precipitate was collected by filtration and purified by vacuum sublimation on a Kugelrohr apparatus. This gave two crystalline solids, that were identified as 4-methylbenzoic acid (0.50 g, 37%) and benzene-1,4-dioic acid (terephthalic acid) (0.08 g, 5%). The remainder was unreacted p-xylene.

The aqueous filtrate containing the ionic liquid was concentrated on a rotary evaporator (80° C. at 50 mmHg) and transferred to the 50 cm$^3$ round bottomed flask, equipped with a magnetic stirrer and reflux condenser. p-Xylene (5.35 g, 50 mmol) and 67% nitric acid (0.90 g, 10 mmol) was added. The mixture was heated under reflux for 5 days, then cooled to room temperature. During this time some of the p-xylene was lost through evaporation. Dilution with water, filtration and sublimation (as above) gave 4-methylbenzoic acid (1.63 g, 24%) and benzene-1,4-dioic acid (terephthalic acid) (0.24 g, 3%). The remainder was unreacted p-xylene.

6. Oxidation of o-xylene

In a 50 cm$^3$ round bottomed flask, equipped with a magnetic stirrer and reflux condenser, was added o-xylene (1.07 g, 10 mmol) and [bmim] [OMs] (1.0 g). 67% Nitric acid (0.45 g, 5 mmol) was cautiously added and the mixture heated under reflux. After 40 hours the mixture was analysed by gas chromatography and gave 42% conversion to 2-methylbenzoic acid and trace of phthalic acid. The remainder was unreacted o-xylene.

7. Oxidation of Propylbenzene

In a 50 cm$^3$ round bottomed flask, equipped with a magnetic stirrer and reflux condenser, was added propylbenzene (1.21 g, 10 mmol) and [bmim] [OMs] (1.0 g). 67% Nitric acid (0.45 g, 5 mmol) was cautiously added and the mixture heated under reflux. After 54, 80 hours the mixture was analysed by gas chromatography and found to give 15% conversion. Three products were identified (GCMS) as: propiophenone, benzoic acid and 3-phenylpentane in the ratio (2:1:trace).

In particular, the present invention relates to a process whereby aromatic compounds bearing an alkyl substituent are oxidised on the alkyl chain on the carbon atom next to the aromatic ring, and where the oxidation is performed in an ionic liquid.

The product of the oxidation reaction is preferably a carboxylic acid or ketone or an intermediate compound in the oxidation such as an aldehyde, or alcohol.

The oxidation is preferably performed in an ionic liquid containing an acid promoter such as methanesulfonic acid.

The oxidation is preferably performed in an ionic liquid containing a nitrogen acid or salt such as nitric acid, nitrous acid, nitrate or nitrite salt. The ionic liquid/acidic promoter combination can be used as a catalyst for the oxidation.

The ionic liquid/acidic promoter can be re-oxidised by an oxidising agent (such as dioxygen in air), and the ionic liquid/acidic promoter can be recycled and reused in further reactions.

The ionic liquid/acidic promoter can be separated from the product by some physical or chemical means such as distillation, steam distillation, azeotropic distillation, sublimation, gravity separation, solvent extraction, crystallisation, supercritical fluid extraction and chromatography.

The present invention also extends to the use of an ionic liquid in the oxidation of an alkyl-aromatic compound, as well as an oxidised alkyl-aromatic compound whenever prepared by a process of the present invention.

References

[1] Hay, A. S.; Blanchard, H. S. *Can. J. Chem.*, 1965, 43, 1306.

[2] Ichikawa, Y.; Yamashita, G.; Tokashiki, M.; Yamaji, T. *Ind. Eng. Chem.*, 1070,62,38 .

[3] Yamazaki, S. *Org.lett.*, 1999,1,2129.

[4] Higashijima, M. *Chem. Lett.* 1999, 1093.

[5] Sasson, Y.; Zappi, G, D.; Neumann, R. *j. Org. Chem.* 1986, 51,2880.

The invention claimed is:

1. A process for the oxidation of an alkyl-aromatic compound comprising admixing the aromatic compound with an oxidising agent or sulfur compound in the presence of an ionic liquid and a nitrogen oxyacid species, wherein the process proceeds at a temperature of0 to 250° C., said ionic liquid comprising an organic anion selected from the group consisting of trifluoroacetate, acetate, methanesulfonate, and combinations thereof1 or an anion based on sulfur, nitrogen, phosphorous, silicon, selenium, tellurium, arsenic, antimony, bismuth, or oxoanions of a metal.

2. The process as claimed in claim 1, wherein the oxidising agent is selected from the group consisting of (i) forms of active oxygen; (ii) hydrated and anhydrous oxides and oxyhalides of nitrogen; (iii) sulfur acid/bases; and combinations thereof.

3. The process as claimed in claim 1, wherein the process is carried out under Bronsted acidic conditions.

4. The process as claimed in claim 1, wherein the nitrogen oxyacid species is a nitrate or nitric acid.

5. The process as claimed in claim 1, wherein the ionic liquid and reaction products are separated by one or more of the processes selected from the group consisting of distillation, sublimation, gravity separation, solvent extraction, crystallisation, supercritical fluid extraction and chromatography.

6. The process as claimed in claim 1, wherein the cation of the ionic liquid is one or more cations selected from the group consisting of ammonium, pyrazolium, 1,3-dialkylimidazolium, pyridinium, alkylpyridinium, poly-alkylpyridinium, alkyl phosphonium and poly-alkyl phosphonium.

7. The process as claimed in claim 6, wherein the cation is a 1,3-dialkylimidazolium cation.

8. The process as claimed in claim 1, wherein the anion is nitrate or methanesulfonate.

9. The process as claimed claim 1, wherein more than one ionic liquid is present.

10. The process as claimed in claim 1, wherein an acid is present.

11. The process as claimed in claim 10, wherein the acid is selected from the group consisting of oxoacids of nitrogen, sulfur, selenium, tellurium, phosphorus, arsenic and antimony; organic acid anions; and combinations thereof.

12. The process as claimed in claim 11, wherein the acid is selected from the group consisting of methanesulfonic acid, nitric acid, nitrous acid and combinations thereof.

13. The process as claimed in claim 10, wherein the ionic liquidlacid combination also acts as a catalyst for the oxidation.

14. The process as claimed in claim 10, wherein the acid is re-oxidised by an oxidising agent.

15. The process as claimed in claim 1, wherein the ionic liquid is [bmin] [OMs] and the oxidising agent is nitric acid.

16. The process as claimed in claim 1, wherein the ionic liquid is [bmin][$NO_3$]and the oxidising agent is methanesulfonic acid.

17. The process as claimed in claim 1, for the oxidation of alkylaromatics, toluene, xylene, or a benzene.

18. The process as claimed in claim 17, for the oxidation of p-xylene.

19. The process as claimed in claim 1, wherein the alkyl chain on the carbon atom next to the aromatic ring in the alkyl-aromatic compound is oxidised.

20. The process as claimed in claim 1, for the preparation of an aldehyde or alcohol.

21. The process according to claim 2, wherein the form of active oxygen is selected from the group consisting of air, dioxygen, peroxide, superoxide and combinations thereof.

22. The process according to claim 2, wherein the sulfur acid/base is sulphuric acid, sulfonic acid, or a combination thereof.

23. The process according to claim 5, wherein the distillation comprises steam distillation or azeotropic distillation.

24. The process according to claim 7, wherein the 1,3-dialkylimidazolium cation is 1-methyl-3-butylimidazolium.

25. The process according to claim 1, wherein the sulfur-containing anion is sulfate, hydrogensulfate, or a combination thereof.

26. The process according to claim 1 wherein the organic anion is trifluoroacetate, acetate, or a combination thereof.

27. The process according to claim 14, wherein the re-oxidising agent is dioxygen in air.

\* \* \* \* \*